United States Patent [19]

Köpe et al.

[11] Patent Number: 4,997,833
[45] Date of Patent: Mar. 5, 1991

[54] ARYLOXY-AMINOALKANES, AND ANTIHYPERTENSIVE USE THEREOF

[75] Inventors: Herbert Köpe; Franz Esser; Wolfram Gaida, all of Ingelheim am Rhein; Wolfgang Hoefke, Wiesbaden; Georg Speck, Ingelheim am Rhein, all of Fed. Rep. of Germany

[73] Assignee: Boehringer Ingelheim K G, Ingelheim am Rhein, Fed. Rep. of Germany

[21] Appl. No.: 375,658

[22] Filed: Jul. 5, 1989

Related U.S. Application Data

[63] Continuation of Ser. No. 101,236, Sep. 25, 1987, abandoned.

[30] Foreign Application Priority Data

Sep. 25, 1986 [DE] Fed. Rep. of Germany ....... 3632544

[51] Int. Cl.$^5$ .................... A61K 31/54; C07D 285/22
[52] U.S. Cl. .................................. 514/223.2; 544/12; 544/13
[58] Field of Search .................. 544/12, 13; 514/223.2

[56] References Cited

U.S. PATENT DOCUMENTS 3,210,347 10/1965 Werner et al. ...................... 544/12

Primary Examiner—Mary C. Lee
Assistant Examiner—Robert C. Whittenbaugh
Attorney, Agent, or Firm—David E. Frankhouser; Mary-Ellen M. Timbers

[57] ABSTRACT

Aryloxy-aminoalkanes useful as antihypertensive agents are described and disclosed.

12 Claims, No Drawings

ARYLOXY-AMINOALKANES, AND ANTIHYPERTENSIVE USE THEREOF

This is a continuation of application Ser. No. 101,236, filed Sept. 25, 1987 now abandoned.

The invention relates to new 1-aryloxy-dihydrobenzothiadiazinylalkylamino-alkanes, the preparation thereof by methods known per se and the use of the new compounds in therapy, particularly for the treatment or prevention of high blood pressure.

The new 1-aryloxy-dihydrobenzothiadiazinylalkylaminoalkane correspond to the general formula

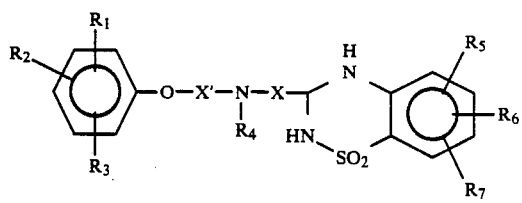

wherein
$R_1$ represents a hydrogen or halogen atom, a lower alkyl, lower alkoxy, lower alkoxy-lower alkyl, lower alkenyl, lower alkenyloxy, cyano, cyano-lower alkyl, hydroxy, trifluoromethyl, nitro, amino, acylamino, aminocarbonylmethyl group, $R_2$ represents a hydrogen or halogen atom, a lower alkyl or lower alkoxy group or an acylamino group $R_3$ represents a hydrogen or halogen atom, an acyl, lower alkyl or lower alkoxy group, $R_2$ and $R_3$ together may also represent a —CH=CH—CH=CH— group or a methylenedioxy group, and also

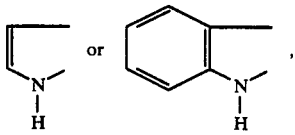

$R_4$ represents a hydrogen atom, a lower alkyl, a lower alkenyl or a lower alkynyl group, $R_5$ represents a chlorine atom or a trifluoromethyl group, $R_6$ represents a chlorine atom or a sulphonamide group, $R_7$ represents a hydrogen atom or a chlorine atom, X represents an alkylene group and X' represents an alkylene group, and the acid addition salts thereof.

The term "halogen atoms" here refers to fluorine, chlorine and bromine. Fluorine and particularly chlorine are preferred.

The lower alkyl or lower alkoxy groups contain 1 to 4, preferably 1 to 3 carbon atoms; the groups with 1 to 2 carbon atoms should be particularly emphasized. Lower-alkenyl and lower-alkynyl groups contain up to 4 carbon atoms and as a rule the double or triple bond is not in the 1 position; allyl and propargyl should be particularly mentioned. Cyanomethyl should be mentioned in particular as the "cyano lower-alkyl". The alkylene group X or X' contains 1 to 8 carbon atoms; preferably X or X' contains 1 to 5 carbon atoms, more particularly 1 to 3 carbon atoms. If the carbon chains consist of a plurality of carbon atoms they may be either branched or unbranched. This also applies to the acyl group in the acylamino group (definition of $R_1$ and $R_2$).

The acyl group (like the acyl group in the definition of $R_3$) contains 1 to 8, preferably 2 to 6 carbon atoms and may be aliphatic or, in the case of $C_7$ and $C_8$, aromatic.

The term "aromatic group" here refers to a phenyl group or a phenyl group which is substituted particularly by halogen atoms, lower alkyl or lower alkoxy groups, or else a benzyl group.

If the compound of formula I contains several substituents with carbon chains, the number of carbon atoms in these chains may be identical or different.

The compounds of formula I may occur as free bases or as acid addition salts. On the basis of their centers of asymmetry they may occur in the form of racemates or mixtures of enantiomers or in the form of the individual enantiomers.

Suitable processes for preparing the new compounds will be described hereinafter.

(a) Reaction of a compound of formula

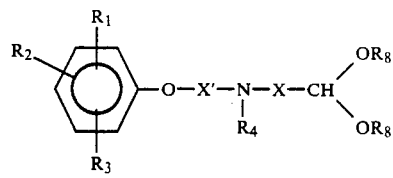

wherein $R_1$, $R_2$, $R_3$, X and X' are defined as hereinbefore and $R_8$ represents an alkyl group or hydrogen, with a compound of formula

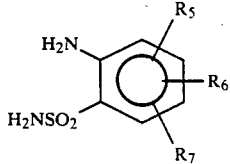

wherein $R_5$ to $R_7$ are defined as hereinbefore.

(b) Reaction of a compound of formula

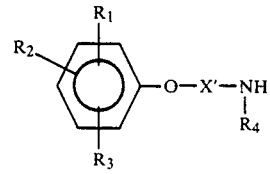

wherein $R_1$ to $R_4$ and X' are defined as hereinbefore, with a compound of formula

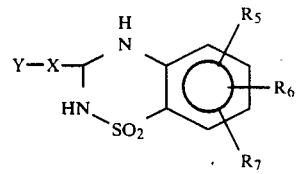

wherein $R_5$ to $R_7$ and X are defined as hereinbefore and Y represents a leaving group such as halogen (Cl, Br or I) or a sulphonic acid ester group.

(c) Reaction of a compound of formula

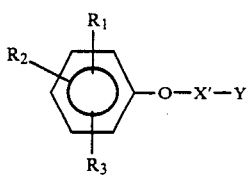

wherein $R_1$ to $R_3$, $X'$ and $Y$ are defined as hereinbefore, with a compound of formula

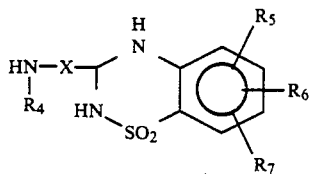

wherein $R_4$ to $R_7$ and $X$ are defined as hereinbefore.

(d) Reaction of a compound of formula

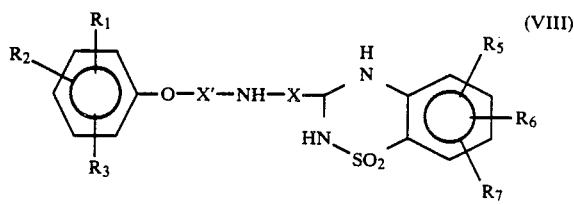

wherein $R_1$ to $R_3$ and $R_5$ to $R_7$, $X$ and $X'$ are defined as hereinbefore, with a compound which is suitable for introducing the group $R_4$.

Examples of suitable compounds of this kind include compounds of formula $$R_4-Z \qquad (IX)$$

wherein $R_4$ is defined as hereinbefore and Z represents a cleavable group such as Cl or Br, or agents for introducing the methyl group, such as dimethylsulphate or formaldehyde/formic acid.

(e) Reaction of a compound of formula

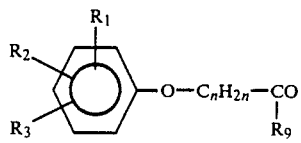

wherein $R_1$ to $R_3$ are defined as hereinbefore and $R_9$ represents a lower alkyl group and n represents an integer from 1 to 6, the sum of the carbon atoms in the group $C_2H_{2n}$—CO—$R_9$ corresponding to that in the $X'$ group of the end product obtained, with a compound of formula

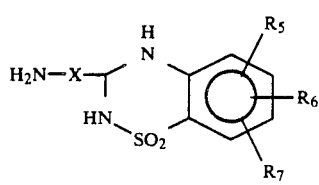

wherein $R_5$ to $R_7$ and $X$ are defined as hereinbefore, under the conditions of hydrogenative amination.

If, according to processes (a) to (e) acid addition salts are initially obtained, these may be converted into free bases or into salts of other acids by conventional methods; bases obtained initially may optionally be converted into acid addition salts.

Processes (a) to (d) are preferably carried out at temperatures between 0° and 100° C., particularly at 40° to 80° C.

The reaction media used may be alcohols or other polar solvents, e.g. methanol, ethanol, isopropanol, dioxan, tetrahydrofuran, optionally in admixture.

The starting compounds for the processes according to the invention are already known or may be prepared by known methods.

The compounds according to the invention have at least one asymmetric carbon atom and occur as racemates or, when several chiral centres are present, as diastereoisomers. These may be synthesized by using optically active starting compounds or may be obtained by recrystallization from suitable solvents or mixtures of solvents.

The 1-aryloxy-dihydrobenzothiadiazinylalkylaminoalkanes of general formula I according to the invention may be converted into their physiologically acceptable acid addition salts in the usual way. Suitable acids include, for example, hydrochloric, hydrobromic, sulphuric, methanesulphonic, maleic, acetic, oxalic, lactic and tartaric acid.

The compounds of general formula I and the physiologically acceptable acid addition salts thereof have shown valuable therapeutic, particularly hypotensive properties in trials on animals and may therefore be used, for example, in the treatment or prevention of high blood pressure in human medicine. They may also be used as intermediate products for preparing other drugs.

The compounds of general formula I which have proved particularly useful are those wherein $R_1$ and $R_2$ each represent a chlorine atom whilst $R_3$ represents hydrogen, $R_4$ represents hydrogen, allyl or propargyl. $R_5$ represents chlorine, $R_6$ represents sulphonamido and $R_7$ is hydrogen or chlorine; or $R_1$ represents a cyano group in the 2 position or a methoxy group in the 3 position or an alkoxyalkyl group in the 4 position; in these cases $R_2$ is hydrogen or acylamino (generally with a total of 4 to 6 carbon atoms), whilst $R_4$ to $R_7$ have the meanings given hereinbefore. $X$ and $X'$ each preferably contain 1 to 3 carbon atoms.

The single dose for the substances according to the invention is from 5 to 300 mg, preferably from 20 to 150 mg (by oral route).

The active substances according to the invention may be made into conventional galenic preparations such as plain or coated tablets, solutions, emulsions, powders, capsules or delayed release forms, and may be produced using the normal pharmaceutical excipients and the usual methods of manufacture. Tablets may be produced, for example, by mixing the active substance or substances with known excipients, e.g. inert diluents such as calcium carbonate, calcium phosphate or lactose, disintegrants such as corn starch or alginic acid, binders such as starch or gelatine, lubricants such as magnesium stearate or talc and/or agents for obtaining delayed release such as carboxypolymethylene, carboxymethyl cellulose, cellulose acetate phthalate or polyvinyl acetate. The tablets may also consist of several layers.

Coated tablets may be produced accordingly by coating cores made in the same way as the tablets with the substances normally used for tablet coating, such as collidone or shellac, gum arabic, talc, titanium dioxide or sugar. In order to obtain delayed release or prevent incompatibilities, the core may also consist of several layers. Similarly, the tablet coating may consist of several layers in order to obtain delayed release, and the excipients mentioned above for the tablets may be used.

Syrups of the active substances or combinations of active substances according to the invention may additionally contain a sweetener such as saccharin, cyclamate, glycerol or sugar and a flavor-enhancing agent, e.g. a flavoring such as vanillin or orange extract.

They may also contain suspension adjuvants or thickeners such as sodium carboxymethylcellulose, wetting agents, e.g. condensation products of fatty alcohols with ethylene oxide, or preservatives such as p-hydroxybenzoates.

Injection solutions are prepared in the usual way, e.g. by adding preservatives such as p-hydroxybenzoates or stabilizers such as complexones and the resulting solutions are transferred into injection vials or ampoules.

Capsules containing one or more active substances or combinations of active substances may be prepared, for example, by mixing the active substances with inert carriers such as lactose or sorbitol and encapsulating the mixture in gelatine capsules.

Suitable suppositories may be produced, for example, by mixing the active substances or combinations of active substances envisaged therefore with conventional carriers such as neutral fats or polyethylene glycol or the derivatives thereof.

The compounds according to the invention are also suitable for combining with other pharmacodynamically active substances such as $\beta$-adrenolytics, diuretics, calcium antagonists or tranquillizers.

EXAMPLES OF FORMULATION

1. Tablets

| Compound according to Example 9 | 40.5 mg |
|---|---|
| Corn starch | 164.0 mg |
| sec. Calcium phosphate | 240.0 mg |
| Magnesium stearate | 1.0 mg |
| | 445.0 mg |

Preparation

The individual components are intensively mixed together and the mixture is granulated in the usual way. The granules are compressed to form tablets weighing 445 mg, each tablet containing 40 mg of active substance.

Instead of the active substances mentioned in this Example, other compounds according to the invention may be used in the same or in a different quantity.

2. Gelatine Capsules

The contents of the capsule have the following composition:

| Compound according to Example 13 | 25.0 mg |
|---|---|
| Corn starch | 175.0 mg |
| | 200.0 mg |

Preparation:

The ingredients of the capsule content are intensively mixed and 200 mg batches of the mixture are packed into suitably sized gelatine capsules. Each capsule contains 25 mg of active substance.

The effect of the compounds according to the invention on blood pressure was investigated on genetically hypertensive rats; the dosage used was 30 mg/kg p.o.

| Example | Lowering of blood pressure in mm Hg/mbar |
|---|---|
| 7 | −63/−84 |
| 9 | −60/−80 |
| 13 | −44/−59 |
| 18 | −56/−75 |
| 22 | −55/−73 |
| 26 | −47/−63 |

Some findings indicate that the blood pressure-lowering effect of the compounds according to the invention is based on a new mechanism of activity. Therefore, a major advantage of the new compounds is that the doctor has a new possible treatment at his disposal if the usual hypotensive agents cannot be used.

The new compounds have a relatively slow onset of activity; their low toxicity is advantageous. Moreover, they have no effect on heart rate and cause no bradycardia.

EXAMPLES OF PREPARATION

Example 1

1-(2-Cyanophenoxy)-3-[(6-chloro-7-sulphonamido-1,1-dioxo-dihydrobenzothiadiazinyl)-3-methylamino]-propane hydrochloride 9.7 g (0.028 mol) of N-3-(2-cyanophenoxy)-1-propylamino-acetaldehyde dimethylacetal hydrobromide are combined with 8 g of 3-chloroanilino-4,6-disulphonamide in 70 ml of ethanol, after the addition of 3 g of p-toluenesulphonic acid, then heated to boiling for 6 hours with stirring. After standing at ambient temperature for 1 day, any undissolved matter is separated off, the filtrate is evaporated down in vacuo and the residue is purified over a silica gel column. Eluant mixture: 700 parts ethyl acetate, 300 parts isopropanol, 10 parts ammonia. After the uniform fractions have been combined and the solvent mixture has been distilled off, the residue remaining is dissolved in 40 ml of acetone and filtered. The filtrate is acidified with alcoholic HCl and a little ether is added. The hydrochloride which crystallizes out is suction filtered and washed with acetone and ether. After drying, 2.6 g of colorless crystals are obtained; M.p.: 145°–147° C.

Example 2

1-(2,4-Dichlorophenoxy)-3-[(6-chloro-7-sulphonamido-1,1-dioxo-dihydrobenzothiadiazinyl)-3-methylamino]-propane hydrochloride 8.3 g (0.021 mol) of N-3-(2.4-dichlorophenoxy)-1-propylamino-acetaldehyde dimethylacetal hydrochloride are suspended in 70 ml of ethanol with stirring and after the addition of 6.1 g (0.021 mol) of 3-chloroanilino-4,6-disulphonamide and 3 g of p-toluenesulphonic acid the mixture is refluxed for 8 hours. After standing for 3 days at ambient temperature, any undissolved matter is separated off, the filtrate is evaporated down in vacuo and the residue is purified over a silica gel column. Eluant mixture: 700 parts ethyl acetate, 300 parts isopropanol, 10 parts ammonia. 1.7 g of pure substance is isolated from the fractions which are found to be uniform in the DC, after the solvent mixture has been distilled off. The compound dissolved in acetone can be obtained as a colorless hydrochloride after the addition of alcoholic HCl (1.2 g);

M.p.: 153°–155° C.

Example 3 was also synthesised analogously to Example 2:

Example 3

1-(3-Methoxyphenoxy)-3-[(6-chloro-7-sulphonamido-1,1-dioxo-dihydrobenzothiadiazinyl)-3-methylamino]-propane hydrochloride M.p.: 116°–118° C.

Example 4

1-(3-Methoxyphenoxy)-N-methyl-3-[(6-chloro-7-sulphonamido-1,1-dioxo-dihydrobenzothiadiazinyl)-3-methylamino]-propane oxalate 5.7 g (0.02 mol) of N-methyl-N-3-(3-methoxyphenoxy)-propylaminoacetaldehyde dimethylacetal are dissolved in 70 ml of dioxan with 5.8 g (0.02 mol) of 3-chloro- anilino-4,6-disulphonamide and then acidified with ethereal HCl. After the dioxan has been distilled off, 2.5 g of p-toluenesulphonic acid and 80 ml of dioxan are added to the residue which is then heated to boiling for 45 minutes with stirring, whereupon oily components are precipitated. The solvent is distilled off in vacuo and the residue is purified over a silica gel column. Solvent mixture: 700 parts ethyl acetate, 300 parts isopropanol, 50 parts ammonia. After evaporation of the eluate the residue is dissolved in acetone and added dropwise to a solution of 5 g of oxalic acid in acetone. After the addition of ether the oxalate crystallizes out as colorless crystals, which are then recrystallized from acetonitrile, to produce 2.1 g of oxalate.

M.p.: 120°–123° C.

The compounds of Examples 5 and 6 are obtained analogously to Example 4.

Example 5

1-(2,4-Dichlorophenoxy)-N-methyl-3-[(6-chloro-7-sulphonamido-1,1-dioxo-dihydrobenzothiadiazinyl)-3-methylamino]-propane hydrochloride M.p.: 165°–167° C.

Example 6

1-(2-Cyanophenoxy)-N-methyl-3-[(6-chloro-7-sulphonamido-1,1-dioxo-dihydrobenzothiadiazinyl)-3-methylamino]-propane hydrochloride M.p.: 153°–156° C.

Example 7

1-(2,6-Dimethylphenoxy)-2-[(6-chloro-7-sulphonamido-1,1-dioxo-dihydrobenzothiadiazinyl)-3-methylamino]-ethane hydrochloride 8.6 g (0.034 mol) of N-2-(2,6-dimethylphenoxy)-1-ethylaminoacetaldehyde dimethylacetal are dissolved in 100 ml of dioxan, 9.7 g (0.034 mol) of 3-chloroanilino-4,6-disulphonamide are added and ethereal HCl is added dropwise. The solvent is distilled off in vacuo, the residue is taken up in 100 ml of dioxan and 4 g of p-toluenesulphonic acid are added. After refluxing for 3 hours, the dioxan is distilled off in vacuo and the residue is purified over a silica gel column. Solvent mixture: 700 parts ethyl acetate, 300 parts isopropanol. After the eluate has been evaporated down the residue is dissolved in acetone, acidified with ethereal HCl and more ether is added until the hydrochloride slowly crystallizes out. 2.9 g of colorless crystals are obtained;

M.p.: 156°–158° C.

Example 8

1-[4-(2-Methoxyethyl)-phenoxy)-2-][(6-chloro-7-sulphonamido-1,1-dioxo-dihydrobenzothiadiazinyl)-3-methylamino]-ethane hydrochloride 10.3 g (0.037 mol) of N-2-[4-(2-methoxyethyl)-phenoxy]-1-ethylaminoacetaldehyde dimethylacetal are dissolved, together with 10.4 g (0.037 mol) of 3-chloroanilino-4,6-disulphonamide, in 100 ml of methanol and ethereal HCl is added. After the solvents have been distilled off the residue is dissolved in 100 ml of dioxan and 4 g of p-toluenesulphonic acid are added. The mixture is refluxed for 5 hours with stirring. After cooling, 8.2 g of crystals are isolated. They are recrystallized from methanol with the addition of ether, to yield 5.7 g of hydrochloride;

M.p.: 197°–198° C.

Example 9

1-(3-Methoxyphenoxy)-2-[(6-chloro-7-sulphonamido-1,1-dioxo-dihydrobenzothiadiazinyl)-3-methylamino]-ethane hydrochloride 8 g (0.031 mol) of N-2-(3-methoxyphenoxy)-1-ethylaminoacetaldehyde dimethylacetal are dissolved in 75 ml of ethanol, 9 g (0.031 mol) of 3-chloranilino-4,6-disulphonamide are added and after the addition of 4 g of p-toluenesulphonic acid the mixture is acidified with alcoholic HCl. After refluxing for 15 hours the solvent is distilled off in vacuo and the residue is purified over a silica gel column. The residue obtained from the eluate is dissolved in acetone and crystallized using alcoholic HCl with the addition of ether. 3.8 g of colorless hydrochloride is obtained;

M.p.: 187°–189° C.

The following substances are obtained analogously to Example 7:

Example 10

1-(3-Methylphenoxy)-2-[(6-chloro-7-sulphonamido-1,1-dioxo-dihydrobenzothiadiazinyl)-3-methylamino]-ethane hydrochloride M.p. 195°–197° C.

Example 11

1-(α-Naphthoxy)-2-[(6-chloro-7-sulphonamido-1,1-dioxo-dihydrobenzothiadiazinyl)-3-methylamino]-ethane hydrochloride M.p.: 169°–172° C.

Example 12

1-(4-Methylphenoxy)-2-[(6-chloro-7-sulphonamido-1,1-dioxo-dihydrobenzothiadiazinyl)-3-methylamino]-ethane hydrochloride M.p.: 201°–203° C.

Example 13

1-(2-Cyanophenoxy)-2-[(6-chloro-7-sulphonamido-1,1-dioxo-dihydrobenzothiadiazinyl)-3-methylamino]-ethane hydrochloride M.p.: 210°–212° C.

Example 14

1-(2,4-Dichlorophenoxy)-2-[(6-chloro-7-sulphonamido-1,1-dioxo-dihydrobenzothiadiazinyl)-3-methylamino]-ethane hydrochloride M.p.: 210°–212° C.

Example 15

1-(3,4-Dimethoxyphenoxy)-2-[(6-chloro-7-sulphonamido-1,1-dioxo-dihydrobenzothiadiazinyl)-3-methylamino]-ethane hydrochloride M.p.: 197°–199° C.

Example 16

1-(3-Methoxyphenoxy)-N-methyl-2-[(6-chloro-7-sulphonamido-1,1-dioxo-dihydrobenzothiadiazinyl)-3-methylamino]-ethane hydrochloride 10.5 g (0.039 mol) of N-methyl-N-2-(3-methoxyphenoxy)-ethylaminoacetaldehyde dimethylacetal are dissolved in 100 ml of ethanol, 4 g of p-toluenesulphonic acid and 11.2 g (0.039 mol) of 3-chloroanilino-4,6-disulphonamide are added and alcoholic HCl is added dropwise. The mixture is refluxed for 12 hours with stirring. After cooling it is evaporated down in vacuo to about 50 ml and made alkaline with ammonia, whereupon a precipitate is formed. After filtration, the filtrate is evaporated to dryness and the residue is purified over a silica gel column. Solvent mixture: 700 parts ethyl acetate, 300 parts isopropanol. 6.1 g of residue are obtained from the eluate, and the residue is dissolved in acetone and stirred into a solution of oxalic acid in acetone. After the addition of ether the oxalate crystallizes out (2.7 g);

M.p.: 168°–170° C.

Example 17

1-(3-Methoxyphenoxy)-N-ethyl-2-[(6-chloro-7-sulphonamido-1,1-dioxo-dihydrobenzothiadiazinyl)-3-methylamino]-ethane hydrochloride 2.05 g (0.004 mol) of 1-(3-Methoxyphenoxy)-2-[(6-chloro-7-sulphonamido-1,1-dioxo-dihydrobenzothiadiazinyl)-methylamino]-ethane hydrochloride are combined with 4 ml of 1N NaOH in 80 ml of methanol.

The solvent is distilled off in vacuo and the residue is combined with a mixture of 1.5 g (0.0054 mol) of ethyl iodide, 400 mg of sodium bicarbonate, 8 ml of dimethylformamide and 20 ml of tetrahydrofuran. The entire mixture is refluxed for 2 hours. After the solvents have been distilled off the residue is purified over a silica gel column. Solvent mixture: 700 parts ethyl acetate, 300 parts isopropanol, 10 parts ammonia. The residue obtained from the eluate is dissolved in acetone, ethereal HCl is added and the hydrochloride is precipitated by the addition of more ether. 0.9 g of amorphous substance are obtained which sinters when heated and then shows signs of decomposition.

Example 18 is synthesized analogously to Example 17:

Example 18

1-(3-Methoxyphenoxy)-N-allyl-2-[(6-chloro-7-sulphonamido-1,1-dioxo-dihydrobenzothiadiazinyl)-3-methylamino]-ethane hydrochloride M.p.: decomposition.

Example 19

1-(3-Methoxyphenoxy)-2-[(6-chloro-7-sulphonamido-1,1-dioxo-dihydrobenzothiadiazinyl)-3-methylamino]-ethane hydrochloride 3.5 g (0.012 mol) of N-2-(3-methoxyphenoxy)-1-ethyl-3-amino-propionaldehyde diethylacetal and 3.4 g (0.012 mol) of 3-chloroanilino-4,6-disulphonamide are dissolved in 60 ml of dioxan, ethereal HCl is added and after the solvent has been distilled off 60 ml of dioxan and 2.3 g of p-toluenesulphonic acid are added. After boiling for 2 hours the solvent is distilled off and the residue is purified over a silica gel column as in Example 17. The isolated base is acidified in acetone with alcoholic HCl and the hydrochloride is obtained by the addition of ether after standing for some time;

M.p.: 167°–169° C.

Compounds 20 and 21 are obtained analogously to Example 19.

Example 20

1-(4-Methoxyphenoxy)-2-[(6-chloro-7-sulphonamido-1,1-dioxo-dihydrobenzothiadiazinyl)-3-ethylamino]-ethane hydrochloride M.p.: 155°–160° C.

Example 21

1-(3-Methoxyphenoxy)-N-methyl-2-[(6-chloro-7-sulphonamido-1,1-dioxo-dihydrobenzothiadiazinyl)-3-ethylamino]-ethane hydrochloride M.p.: Decomposition.

Example 22

1-(3-Methoxyphenoxy)-2-[(6-trifluoromethyl-7-sulphonamido-1,1-dioxo-dihydrobenzothiadiazinyl)-3-ethylamino]-ethane hydrochloride 1.6 g (0.006 mol) of N-2-(3-methoxyphenyl)-1-ethyl-2-amino-acetaldehyde dimethylacetal are dissolved in 400 ml of dioxan and, after the addition of 2 g (0.006 mol) of 3-chloroanilino-4,6-disulphonamide, alcoholic HCl is added. After refluxing for 1 hour the mixture is made alkaline with ammonia, evaporated down in vacuo and the residue is purified over a silica gel column as in Example 17. The base is dissolved in acetone, ethereal HCl is added and the hydrochloride is obtained in the form of colorless crystals by the addition of ether (1.3 g);

M.p.: 187°–190° C.

The following compound is obtained analogously to Example 22:

Example 23

1-(3-Methoxyphenoxy)-2-[(6-trifluoromethyl-7-sulphonamido-1,1-dioxo-dihydrobenzothiadiazinyl)-3-methylamino]-ethane hydrochloride M.p.: amorphous substance, decomposition.

Example 24

1-(3-Methoxyphenoxy)-2-[(6,7-dichloro-1,1-dioxo-dihydrobenzothiadiazinyl)-3-methylamino]-ethane hydrochloride 4.82 g (0.02 mol) of 3,4-Dichloranilino-6-sulphonamide are stirred into 75 ml of dioxan, 5.1 g (0.02 mol) of N-2-(3-methoxyphenoxy)-1-ethyl-2-aminoacetaldehyde dimethylacetal are added and ethereal HCl is added dropwise. After the solvents have been distilled off 75 ml of dioxan and 2 g of p-toluenesulphonic acid are added. The mixture is refluxed for 1 hour. The substance precipitated is isolated, dissolved in methanol, ammonia is added, the resulting mixture is filtered and the hydrochloride is precipitated by the addition of ethereal HCl, 2.9 g of crystals are obtained;
M.p.: 182°–183° C.

The compounds of the Examples which follow were obtained analogously:

Example 25

1-(4-Methoxyethylphenoxy)-2-[(6,7-dichloro-1,1-dioxo-dihydrobenzothiadiazinyl)-3-methylamino]-ethane hydrochloride M.p.: 187°–189° C.

Example 26

1-(4-Methoxyethylphenoxy)-2-[(6,8-dichloro-1,1-dioxo-dihydrobenzothiadiazinyl)-3-methylamino]-ethane hydrochloride M.p.: 195°–197° C.

Example 27

1-(3-Methoxyphenoxy)-2-[(6,8-dichloro-1,1-dioxo-dihydrobenzothiadiazinyl)-3-methylamino]-ethane hydrochloride M.p.: 200°–201° C.

Example 28

1-(3-Methoxyphenoxy)-2-[(5,6-dichloro-7-sulphonamido-1,1-dioxo-dihydrobenzothiadiazinyl)-3-methylamino]-ethane hydrochloride M.p.: 190°–192° C.

Example 29

1-(4-Methoxyethoxyphenoxy)-2-[(5,6-dichloro-7-sulphonamido-1,1-dioxo-dihydrobenzothiadiazinyl)-3-methylamino]-ethane hydrochloride M.p.: 185°–188° C.

Example 30

1-(2-Allylphenoxy)-2-[(6-chloro-7-sulphonamido-1,1-dioxo-dihydrobenzothiadiazinyl)-3-methylamino]-ethane hydrochloride M.p.: 144°–147° C.

Example 31

1-(3-Nitrophenoxy)-2-[(6-chloro-7-sulphonamido-1,1-dioxo-dihydrobenzothiadiazinyl)-3-methylamino]-ethane hydrochloride M.p.: 184°–186° C.

Example 32

1-(2,6-Dimethylphenoxy)-2-[(6-chloro-7-sulphonamido-1,1-dioxo-dihydrobenzothiadiazinyl)-3-methylamino]-ethane hydrochloride M.p.: 192°–194° C.

Example 33

1-(2-Allyloxyphenoxy)-2-[(6-chloro-7-sulphonamido-1,1-dioxo-dihydrobenzothiadiazinyl)-3-methylamino]-propane hydrochloride M.p.: 152°–154° C.

Example 34

1-(3-Methoxyphenoxy)-2-[(6-chloro-7-sulphonamido-1,1-dioxo-dihydrobenzothiadiazinyl)-3-methylamino]-propane hydrochloride M.p.: 189°–192° C.

Example 35

1-(2-Cyanophenoxy)-2-[(6-chloro-7-sulphonamido-1,1-dioxo-dihydrobenzothiadiazinyl)-3-methylamino]-propane hydrochloride M.p.: 193°–194° C.

Example 36

1-(2-Cyano-4-isobutyroylamidophenoxy)-2-[(6-chloro-7-sulphonamido-1,1-dioxo-dihydrobenzothiadiazinyl)-3-methylamino]-ethane hydrochloride M.p.: 140°–142° C.

Example 37

1-(2-Bromophenoxy)-2-[(6-chloro-7-sulphonamido-1,1-dioxo-dihydrobenzothiadiazinyl)-3-methylamino]-ethane hydrochloride M.p.: 155°–158° C.

Example 38

1-(3,4-Methylenedioxyphenoxy)-2-[(6-chloro-7-sulphonamido-1,1-dioxo-dihydrobenzothiadiazinyl)-3-methyl-amino]-ethane hydrochloride M.p.: 211°–213° C.

Example 39

1-(2,4,5-Trichlorophenoxy)-2-[(6-chloro-7-sulphonamido-1,1-dioxo-dihydrobenzothiadiazinyl)-3-methylamino]-ethane hydrochloride M.p.: 174°–177° C.

Example 40

1-(2-Allylphenoxy)-N-methyl-2-[(6-chloro-7sulphonamido-1,1-dioxo-dihydrobenzothiadiazinyl)-3-methylamino]-ethane hydrochloride M.p.: 156°–159° C.

Example 41

1-(2-Allyloxyphenoxy)-N-methyl-2-[(6-chloro-7-sulphonamido-1,1-dioxo-dihydrobenzothiadiazinyl)-3-methyl-amino]-ethane hydrochloride M.p.: 164°–165° C.

Example 42

1-(2-Bromophenoxy)-N-methyl-2-[(6-chloro-7-sulphonamido-1,1-dioxo-dihydrobenzothiadiazinyl)-3-methylamino]-ethane hydrochloride M.p.: 168°–169° C.

Example 43

1-(3-Nitrophenoxy)-N-methyl-2-[(6-chloro-7-sulphonamido-1,1-dioxo-dihydrobenzothiadiazinyl)-3-methylamino]-ethane hydrochloride M.p.: 169°–171° C.

Example 44

1-(4-Hydroxyphenoxy)-2-[(6-chloro-7-sulphonamido-1,1-dioxo-dihydrobenzothiadiazinyl)-3-methylamino]-ethane hydrochloride M.p.: 179°–181° C.

Example 45

1-(3-Bromophenoxy)-2-[(6-chloro-7-sulphonamido-1,4-dioxo-dihydrobenzothiadiazinyl)-3-methylamino]-ethane hydrochloride M.p.: 182°–184° C.

Example 46

1-(2-Methoxyphenoxy)-2-[(6-chloro-7-sulphonamido-1,1-dioxo-dihydrobenzothiadiazinyl)-3-methylamino]-ethane hydrochloride M.p.: 220°–223° C.

Example 47

1-(2-Cyanomethyl-5-methoxyphenoxy)-2-[(6-chloro-7-sulphonamido-1,1-dioxo-dihydrobenzothiadiazinyl)-3-methylamino]-ethane hydrochloride M.p.: 184°–186° C.

Example 48

1-(2-Methoxyphenoxy)-N-n-propyl-2-[(6-chloro-7-sulphonamido-1,1-dioxo-dihydrobenzothiadiazinyl)-3-methylamino]-ethane hydrochloride M.p.: 145°–148° C.

Example 49

1-(3-Ethoxyphenoxy)-2-[(6-chloro-7-sulphonamido-1,1-dioxo-dihydrobenzothiadiazinyl)-3-methylamino]-ethane hydrochloride M.p.: 177°–180° C.

Example 50

1-(Phenoxy)-2-[(6-chloro-7-sulphonamido-1,1-dioxo-dihydrobenzothiadiazinyl)-3-methylamino]-ethane hydrochloride M.p.: 193°–195° C.

Example 51

1-(4-Ethoxyphenoxy)-2-[(6-chloro-7-sulphonamido-1,1-dioxo-dihydrobenzothiadiazinyl)-3-methylamino]-ethane hydrochloride M.p.: 193°–196° C.

Example 52

1-(3-Methoxyphenoxy)-N-propargyl-2-[(6-chloro-7-sulphonamido-1,1-dioxo-dihydrobenzothiadiazinyl)-3-methylamino]-ethane hydrochloride M.p.: 160°–162° C.

Example 53

1-(2,4-Dichlorophenoxy)-N-propargyl-2-[(6-chloro-7-sulphonamido-1,1-dioxo-dihydrobenzothiadiazinyl)-3-methylamino]-ethane hydrochloride M.p.: 153°–155° C.

Example 54

1-(a-Naphthoxy)-N-propargyl-2-[(6-chloro-7-sulphonamido-1,1-dioxo-dihydrobenzothiadiazinyl)-3-methylamino]-ethane hydrochloride M.p.: 86°–88° C.

Example 55

1-(2,4-Dichlorophenoxy)-2-[(6,7-dichloro-1,1-dioxo-dihydrobenzothiadiazinyl)-3-methylamino]-propane hydrochloride M.p.: 190°–192° C.

Example 56

1-(2,4-Dichlorophenoxy)-2-[(5,6-dichloro-7-sulphonamido-1,1-dioxo-dihydrobenzothiadiazinyl)-3-methylamino]-propane hydrochloride M.p.: 170°–172° C.

Example 57

1-(4-Methoxyethylphenoxy)-N-propargyl-2-[(6-chloro-7-sulphonamido-1,1-dioxo-dihydrobenzothiadiazinyl)-3-methylamino]-ethane hydrochloride M.p.: 168°–171° C.

The following compounds may also be prepared using the processes according to the invention:

1-(4-Carbazolyloxy)-2-[(6-chloro-7-sulphonamido-1,1-dioxo-dihydrobenzothiadiazinyl)-3-methylamino]-ethane hydrochloride 1-(4-Indolyloxy)-2-[(6-chloro-7-sulphonamido-1,1-dioxo-dihydrobenzothiadiazinyl)-3-methylamino]-ethane hydrochloride 1-(2-Acetyl-4-butyroylamidophenoxy)-2-[(6-chloro-7-sulphonamido-1,1-dioxo-dihydrobenzothiadiazinyl)-3-methylamino]-ethane hydrochloride 1-(3-Hydroxyphenoxy)-2-[(6-chloro-7-sulphonamido-1,1-dioxo-dihydrobenzothiadiazinyl)-3-methylamino]-ethane hydrochloride 1-(2-Allylphenoxy)-2-[(6-chloro-7-sulphonamido-1,1-dioxo-dihydrobenzothiadiazinyl)-3-methylamino]-propane hydrochloride 1-(2-Allyloxyphenoxy)-2-[(6-chloro-7-sulphonamido-1,1-dioxo-dihydrobenzothiadiazinyl)-3-methylamino]-propane hydrochloride 1-(2-Bromophenoxy)-2-[(6-chloro-7-sulphonamido-1,1-dioxo-dihydrobenzothiadiazinyl)-3-methylamino]-propane hydrochloride 1-(3-Nitrophenoxy)-2-[(6-chloro-7-sulphonamido-1,1-dioxo-dihydrobenzothiadiazinyl)-3-methylamino]-propane hydrochloride

What is claimed is:
1. A compound of formula

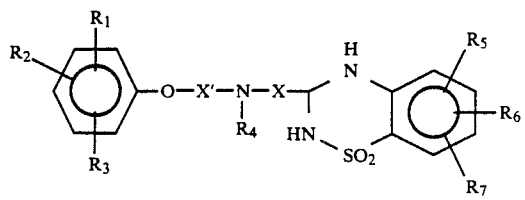

wherein
- $R_1$ is hydrogen, halo, $C_{1-4}$ alkyl, $C_{1-4}$ alkoxy, $C_{1-4}$-alkoxy-($C_{1-4}$-alkyl), alkenyl with up to 4 carbon atoms, alkenyloxy with up to 4 carbon atoms, cyano, cyano-($C_{1-4}$-alkyl), hydroxy, trifluoromethyl, nitro, amino, $C_{2-6}$ alkylcarbonylamino or aminocarbonylmethyl,
- $R_2$ is hydrogen, halo, $C_{1-4}$ alkyl, $C_{1-4}$ alkoxy or $C_{2-6}$ alkylcarbonylamino,
- $R_3$ is hydrogen, halo, $C_{2-6}$ alkylcarbonyl, $C_{1-4}$ alkyl, or $C_{1-4}$ alkoxy or $R_2$ and $R_3$ together are —CH═CH—CH═CH—, methylenedioxy,

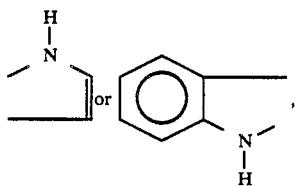

- $R_4$ is hydrogen, $C_{1-4}$ alkyl, alkenyl with up to four carbon atoms or alkinyl with up to four carbon atoms,
- $R_5$ is chloro or trifluoromethyl,
- $R_6$ is chloro or sulphonamide,
- $R_7$ is hydrogen or chloro,
- X is $C_{1-8}$ alkylene,
- X' is $C_{1-8}$ alkylene, or an acid addition salt thereof.

2. A compound of formula

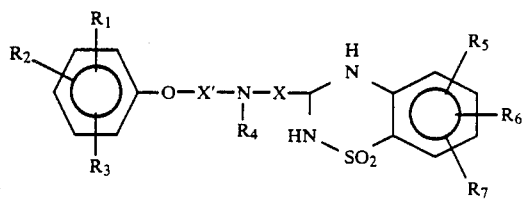

wherein
- $R_1$ is chloro, bromo, CN, $NO_2$, OH, $CH_2CN$, methoxy, ethoxy, methyl, ethyl, allyl, allyloxy, methoxyethyl or hydrogen,
- $R_2$ is hydrogen, chloro, methyl, methoxy or $C_{2-6}$ alkyl carbonylamino,
- $R_3$ is hydrogen, chloro or $C_{2-6}$ alkylcarbonyl, or $R_2$ and $R_3$ together are —CH═CH—CH═CH; —O—$CH_2$—O—, —CH═CH—NH— or

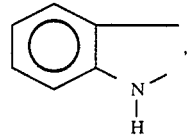

- $R_4$ is hydrogen, $C_{1-3}$ alkyl, allyl or propargyl,
- $R_5$ is chloro or trifluoromethyl,
- $R_6$ is chloro or sulphonamide,
- $R_7$ is hydrogen
- X is $(CH_2)_n$, wherein n is 1 or 2,
- X' is $(CH_2)_m$, wherein m is 1, 2 or 3, or an acid addition salt thereof.

3. 1-(3-Methoxyphenoxy)-2-[(6-chloro-7-sulphonamido-1,1-dioxo-dihydrobenzothiadiazinyl)-3-methylamino]-ethane or an acid addition salt thereof.

4. 1-(2-Cyanophenoxy)-2-[(6-chloro-7-sulphonamido-1,1-dioxo-dihydrobenzothiadiazinyl)-3-methylamino]-ethane or an acid addition salt thereof.

5. 1-(3-Methoxyphenoxy)-2-[(6-trifluoromethyl-7-sulphonamido-1,1-dioxo-dihydrobenzothiadiazinyl)-3-ethylamino]-ethane or an acid addition salt thereof.

6. 1-(2,6-Dimethylphenoxy)-2-[(6-chloro-7-sulphonamido-1,1-dioxo-dihydrobenzothiadiazinyl)-3-methylamino]-ethane or an acid addition salt thereof.

7. 1-(3-Methoxyphenoxy)-N-allyl-2-[(6-chloro-7-sulphonamido-1,1-dioxo-dihydrobenzothiadiazinyl)-3-methylamino]-ethane or an acid addition salt thereof.

8. 1-(4-Methoxyethylphenoxy)-2-[(6,8-dichloro-1,1-dioxo-dihydrobenzothiadiazinyl)-3-methylamino]-ethane or an acid addition salt thereof.

9. A pharmaceutical composition of matter useful in the treatment of hypertension in warm-blooded animals comprising a pharmaceutically active amount of a compound as recited in claim 1 together with a pharmaceutically acceptable carrier.

10. A pharmaceutical composition of matter useful in the treatment of hypertension in warm-blooded animals comprising a pharmaceutically active amount of a compound as recited in claim 2 together with a pharmaceutically acceptable carrier.

11. A method for treatment of hypertension in a warm-blooded animal which comprises administering to said animal an effective amount of a compound as recited in claim 1.

12. A method for treatment of hypertension in a warm-blooded animal which comprises administering to said animal an effective amount of a compound as recited in claim 2.

* * * * *